United States Patent [19]

Lai

[11] Patent Number: 5,013,836

[45] Date of Patent: May 7, 1991

[54] PROCESS FOR METHYLATING A HINDERED NITROGEN ATOM IN A POLYSUBSTITUTED DIAZACYCLOALKAN-2-ONE

[75] Inventor: John T. Lai, Broadview Heights, Ohio

[73] Assignee: The B. F. Goodrich Company, Brecksville, Ohio

[21] Appl. No.: 439,408

[22] Filed: Nov. 21, 1989

[51] Int. Cl.$^5$ .................. C07D 241/08; C07D 241/44; C07D 243/10; C07D 243/14

[52] U.S. Cl. ..................................... 540/512; 540/492; 540/504; 540/514; 540/598; 544/113; 544/198; 544/231; 544/354; 544/357; 544/384

[58] Field of Search .............. 540/492, 504, 512, 514, 540/598; 544/113, 198, 231, 354, 357, 384

[56] References Cited

FOREIGN PATENT DOCUMENTS 226943 4/1984 Czechoslovakia .
2492367 4/1982 France .
2194237A 3/1988 United Kingdom .

OTHER PUBLICATIONS

"Methylation of Amines with Formaldehyde", Organic Reactions, vol. V by M. L. Moore, 1952, pp. 323–325, John Wiley & Son, New York.

Primary Examiner—Richard L. Raymond
Attorney, Agent, or Firm—Alfred D. Lobo; Nestor W. Shust

[57] ABSTRACT

The difficulty of methylating a hindered piperidinyl, piperazinyl, or diazepinyl group with an Eschweiler-Clarke ("E-C") procedure without using a large molar excess (more than double) of formaldehyde is surprisingly found to be non-existent in the case of a diazacycloalkan-2-one group with a hindered $N^4$- or $N^5$-atom of its NH group which is to be methylated. The $N^4$- or $N^5$-atom of a polysubstituted diazacycloalkan-2-one group ("DCA") is substantially stoichiometrically converted even when a conventional E-C procedure is starved of HCHO, that is, with a much smaller molar excess of formaldehyde than deemed necessary. The effective molar ratio of NH groups: HCHO in the starved E-C process is in the range from 1:1 to 1:1.5, in the presence of enough formic acid to function both as reactant and solvent not only for a DCA-containing complex amine ("starting amine") to be methylated, but also for the methylated amine (product). Such a starting amine may have one or more DCA substituents which, in turn, may be connected to any other structure. Because this process is starved of at least HCHO, and usually both HCHO and HCOOH, it is referred to herein as the "starved E-C process". Upon completion of the reaction any excess HCOOH is neutralized with aqueous alkali, and the product separates from the reaction mass. Though the starting amine is often substantially soluble in water, it usually becomes substantially insoluble after it is methylated. Less than 5% of product is lost in the aqueous wash.

21 Claims, 1 Drawing Sheet

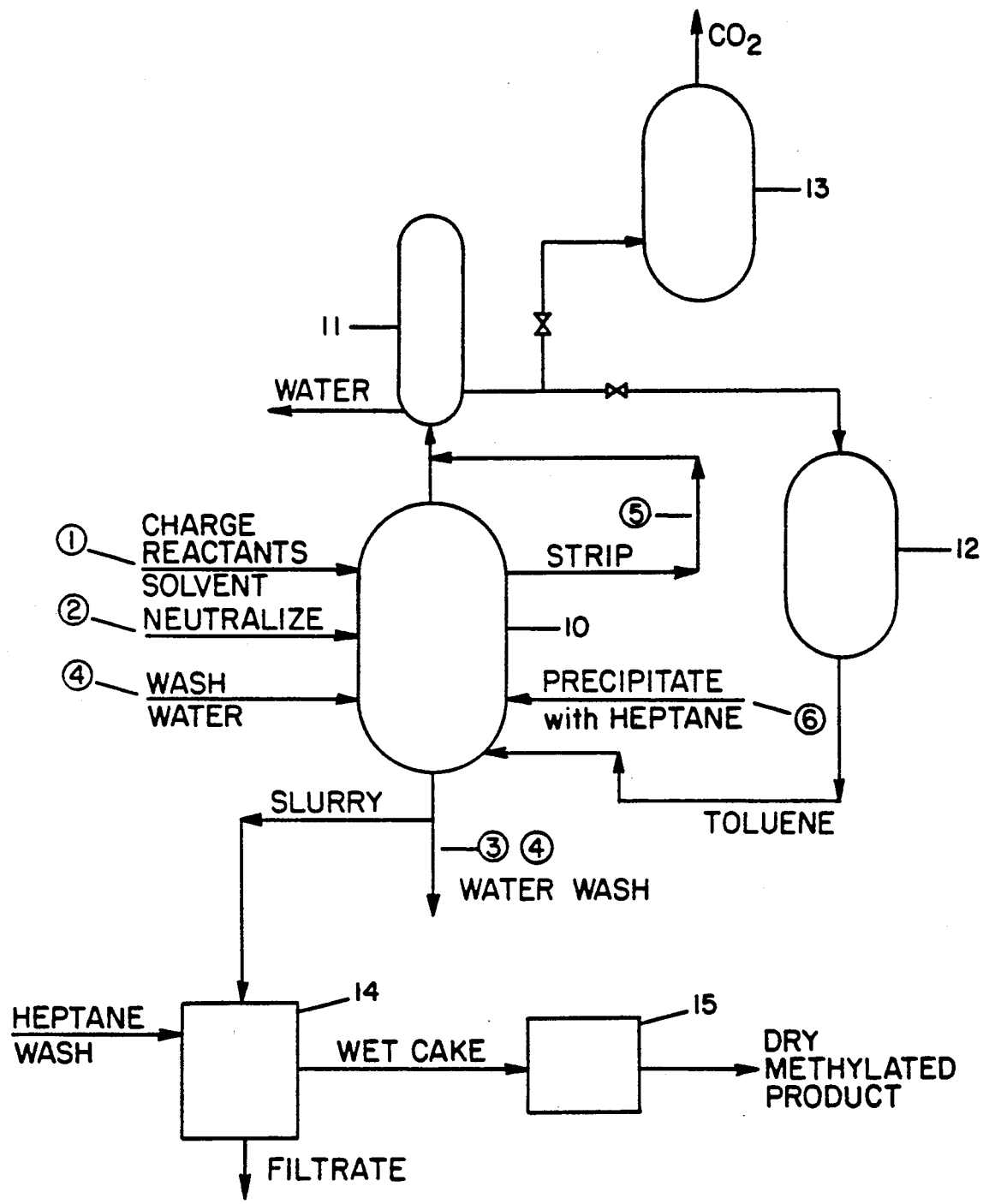

PROCESS FOR METHYLATING A HINDERED NITROGEN ATOM IN A POLYSUBSTITUTED DIAZACYCLOALKAN-2-ONE

BACKGROUND OF THE INVENTION

For several decades, the use of the Eschweiler-Clarke ("E-C" for brevity) reaction has been used in laboratory procedures for the methylation of simple acyclic and cyclic amines, with excellent results, the reaction proceeding essentially quantitatively with only a relatively small excess of formaldehyde (HCHO) and enough formic acid (HCOOH) to solvate the amine reactant, typically from a 2-fold to 4-fold molar excess of HCOOH. If a much larger excess of HCHO and HCOOH is necessary, the E-C reaction is not used, as far as we know, commercially. The reason is that it is impractical to recover the unused excess reactants.

Because of the convenient and economical way in which the E-C reaction can introduce a methyl substituent on an amine N atom, the reaction has attracted particular attention for the methylation of the hindered N atom of hindered piperidyl, piperazinyl, piperazin-2-one, diazepine and diazepin-2-one groups, in stabilizer compounds commonly referred to as "hindered amines". Except that, because of the highly hindered N atom to be methylated, the reaction is usually carried out in the laboratory with at least a 2-fold molar excess of HCHO and a much larger excess of HCOOH. Most of the excess HCOOH is recoverable for reuse by an economical distillation but excess of HCHO is wasted. Thus, with a 2-fold molar excess of HCHO, one mole is wasted for each mole used. This is too large an excess of HCHO to be economical. I decided to investigate solutions to this problem, namely the methylation of the hindered N atom in hindered amine light and heat stabilizers for organic compounds.

In UK Pat. appl. GB 2,194,237 (Mar. 2, '88) piperidyl-containing compounds were methylated using the E-C procedure. Example 1 discloses preparation of a tetramine containing plural triazine rings, each substituted with two pentamethylated piperidyl substituents. The amine to be methylated is $N^1,N^2,N^3, N^4$-tetrakis-[2,4-bis[N-(2,2,6,6-tetramethyl-4-piperidyl)-n-butylamino]-1,1,3,5-triazin-6-yl]-4,7-diazadecane-1,10-diamine; it has 2 terminal -NH groups and 8 tetramethyl-4-piperidyl substituents, each with a >NH group. To a solution of 0.02 moles of this amine in 100 ml of water is added 0.4 moles of formic acid (two-fold molar excess) and 0.4 moles of a 40% aqueous formaldehyde solution (two-fold molar excess). The solution is heated under reflux for 8 hr; after cooling to room temperature, an additional amount of 0.2 moles (stoichiometric for all NH groups to be methylated) of 40% formaldehyde is added and the solution refluxed for an additional 5 hr. Repeating this reaction with a simpler piperidyl-substituted compound and a two-fold excess of HCHO and HCOOH, I found that methylation proceeded with excellent conversion, albeit relatively slowly. However, when the reaction was starved of HCHO by decreasing the molar excess of HCHO to 50% (in steps, from 200%) the reaction mass was so difficult to work up, that a NMR (nuclear magnetic resonance) mass spectrographic analysis of the concentrated reaction mass had to done, and this indicated less than 50% methylation of the >NH group irrespective of how much HCOOH was used.

Several methylated piperazine- and piperazin-2-one-containing stabilizers have been disclosed in Japanese Pat. application No. 63-86711 published Apr. 18 1988. In such PSP-containing compounds, the hindered $N^4$ atom in the diazacycloalkan-2-one ring is substituted at both the 3-and 5- positions. The $N^4$ atom is hindered in all such PSPs. This $N^4$ atom is termed "the hindered N atom" because it is flanked by disubstituted 3- and 5-carbon atoms, either or both of which may have a spiro substituent. Homologous (with the piperazin-2-ones) are diazepin-2-one compounds containing a seven-membered diaza ring. The polysubstituted piperazin-2-one ("PSP") and diazepin-2-one substituents are each diazacycloalkan-2-one substituents which are together referred to herein by the acronym "DCA", for convenience.

A polysubstituted diazacycloalkan-2-one and compounds containing one or more DCA substituents are "DCA-containing" compounds referred to herein as "complex amines". In the Japanese reference, methylated PSP stabilizers are said to improve the color of polyacetals. There is no teaching of how such methylated compounds were prepared, but because such methylated stabilizers are not commercially available, it is expected they were synthesized in the laboratory. Since I was particularly interested in methylating DCA-containing compounds, and more particularly, PSP-containing compounds, my efforts were directed to converting an uneconomical laboratory process for methylating such compounds to an economical one.

The process of this invention exploits the peculiar and unique susceptibility of a DCA group to a starved E-C procedure. The unique configuration of a DCA group imbues it with characteristics which permit easy methylation of only the NH groups in the DCA, while failing to methylate other -NH groups which may be present in complex amines.

Examples of DCAs are those referred to in U.S. Pat. No. 4,190,571 the disclosure of which is incorporated by reference thereto as if fully set forth herein, and the aforementioned Japanese 63-86711. Illustrative of DCA-containing compounds are (a) triazine compounds having PSP substituents such as those disclosed in U.S. Pat. Nos. 4,480,092; 4,629,752; and, 4,639,479 (referred to as "PIP-T" compounds); and (b) N-(substituted)-α-(3,5-dialky-4-hydroxyphenyl)-α,α-disubstituted acetamides disclosed in U.S. Pat. No. 4,780,495 (referred to as "3,5-DHPZNA" compounds); the disclosure of each of which foregoing references is incorporated by reference thereto as if fully set forth herein. Methylated PSPs, 3,5-DHPZNAs and PIP-Ts, in each of which the NH groups are methylated, are excellent stabilizers for polyoxymethylene resins, particularly polyacetals.

A typical E-C process is described under the heading "Methylation of Amines with Formaldehyde" in Organic Reactions, Vol V by M. L. Moore, pg 307 et seq., as follows: "One molecular proportion (or slight excess) of formaldehyde and two to four molecular proportions of formic acid are used for each methyl group introduced, indicating that it is mainly the formic acid that supplies the hydrogen involved in the reduction. The reaction is carried out on a steam bath." The HCHO contributes the carbon atom of the methyl group, the HCOOH solvates the amine reactant and provides the hydrogen (proton) for reduction.

This typical E-C reaction, carried out with a primary or secondary amine, results in the methylated amine when the reactants are heated for several hours after the evolution of gas has ceased. The formic acid functions as both a co-reactant and a solvent. The function of formic acid as a solvent is particularly important when the amine to be methylated is poorly soluble in water.

Unhindered amines such as benzylamine and secondary amines such as piperidine and piperazine are expected to be methylated with a slight excess of HCHO to give almost theoretical conversion to the corresponding methylated amines, and in practice, provides a highly acceptable conversion, even if not quantitative. But because hindered amines are so highly hindered, they are not expected to provide essentially complete conversion, are expected to require a large excess of HCHO. The overall yield of the reaction is further reduced by the difficulty of recovering the desired product from the reaction mass ("work-up"). The result is an unacceptably low yield from a high-priced complex amine starting material, and the low yield makes the E-C process uneconomical.

In a text-book procedure for a typical E-C reaction (see Moore, supra pg 323), benzylamine (1 mole) is added with cooling, to 5 moles of 90% formic acid. Then 2.2 moles of 35% formaldehyde solution is added, and the mixture is heated on a steam bath under reflux for 2 to 4 hours after evolution of gas has ceased (8 to 12 hr in all). Slightly more than 1 mole of concentrated hydrochloric acid is then added and the formic acid and any excess formaldehyde are evaporated on a steam bath. The colorless residue is dissolved in water and made alkaline by the addition of 25% aqueous sodium hydroxide, and distilled over sodium. The product, N,N-dimethylbenzylamine is recovered in excellent yield.

Carrying out this reaction commercially is burdened with the costs of recovering the large excess of formaldehyde or formic acid, or both. For example, Czech appln. No. 82/5562 filed July 21, 1982 discloses treating the methylated product with HCl, then distilling under vacuum to remove volatiles. The yield was 66–70% which is commercially unacceptable because of the high cost of a DCA-containing amine to be methylated. Such a distillation process still leaves the problem of separating the large excess of formic acid from the formaldehye.

Separating formaldehyde and formic acid as aqueous solutions of chosen concentration (which may later be diluted) by distillation, is not practical because of the too-close boiling points. For example, USSR appln No. 80/22299, filed Oct 10, 1980 discloses distillation in a column the pressure at the top and bottom of which was 20 mm and 2 atm respectively.

My process is applicable only to the methylation of DCA-containing compounds and not to piperidines or diazacycloalkanes because the latter two are not susceptible to methylation when starved of HCHO. It was surprising that only a DCA group can be methylated with only a bare excess of formaldehyde, much less than the amount one would typically expect to use in a conventional E-C reaction (hence my process is referred to as the "starved E-C process"). The amount of water present during the starved E-C reaction is not critical except for the effect on the time required to complete the reaction. In general, the more dilute the reaction mass, the longer the time for the reaction, and in a commercial process, it is generally desired to run under conditions which provide maximum reactor productivity.

Neither could it have been foreseen that, after the reaction is completed and the formic acid neutralized with sufficient aqueous alkali to make the reaction mass basic ("basified"), the methylated product would separate from solution, and would be so insoluble in water that it could be washed with water without sacrificing any more than 1% of its weight. This ability to wash out essentially all impurities from the solvent phase, including unreacted formaldehyde, formic acid and salt formed upon neutralization, enhances the efficiency of, and vastly simplifies the recovery procedure for the methylated product. It will be recognized that not all methylated complex amines will be so insoluble as to lose less than 5% upon repeated washing with water, so that my process is specifically directed to those which do.

Irrespective of the dilution of the reaction mass with water, the starved E-C reaction is carried out at above about 60° C., and $CO_2$ formed during the reaction is driven off. A higher temperature shortens the time for the reaction, producing the methylated DCA substantially quantitatively, typically in less than 8 hr.

It will be evident from the foregoing, that the steps under which adequate conversion is obtained in a reasonable amount of time, and the steps of a "work-up", taking advantage of the substantial insolubility of the methylated complex amine in water (under process conditions provided in the recovery system), must together provide a high enough yield of essentially pure product to make the process commercially successful.

The difficulty of methylating the hindered N atom of a piperidyl group, Piccinelli et al (Eur. Pat. appln. 0319480 published June 7, 1989) used an alkylbenzene solvent in a modification of the usual E-C procedure. They methylated triazine compounds containing 2,2,6,6-tetramethylpiperidyl groups. But there is no indication of either what percentage of the piperidyl groups were methylated, or what the yields might have been.

My process relates specifically to methylating the hindered N atom of a DCA group by starving the well-known E-C reaction of HCHO, yet achieving essentially stoichiometrically complete conversion of the >NH group(s) in any DCA-containing compound. This process takes advantage of the discovery that the NH group in a DCA is uniquely susceptible to methylation without a large excess of HCHO. This discovery provides the basis for a commercial process.

SUMMARY OF THE INVENTION

It has been discovered that the hindered N atom of a polysubstituted diazacycloalkan-2-one ("DCA"), whether a diazepin-2-one or a piperazin-2-one ("PSP"), may be methylated with substantially stoichiometrically complete conversion by using a "starved" Eschweiler-Clarke ("E-C") procedure. This procedure starves the reaction of HCHO. In some instances only a molar amount of HCHO results in complete conversion of the starting amine to methylated product. The starved E-C process comprises adding enough formic acid as will form a solution with the DCA under reaction conditions, and no more than a bare molar excess of formaldehyde, so as to produce a $N^4$- or $N^5$-methylated amine without using any solvent. The formic acid reactant serves as solvent. The amount of water present is not critical and the methylation of the hindered $N^4$- or $N^5$-atom will be substantially stoichiometric under either "dilute" (more than 30% by weight of the reaction mass is water) or "concentrated" (from about 1% to 30% by weight is water) conditions. After neutralization of the reaction mass, the product separates spontaneously, generally as a water-insoluble solid which can be washed with water without significant loss, typically providing an yield in excess of 90%.

It is therefore a general object of this invention to provide a starved E-C process for methylating a DCA or DCA-containing complex amine ("starting amine") using less than 2 mols HCHO per >NH group, preferably no more than 50% over stoichiometric of HCHO, which excess fails to methylate the >NH group of a polysubstituted piperidine, piperazine or diazepine (hindered amine), so as to produce more than 50% conversion (molar) of the starting amine.

It is also a general object of this invention to provide a starved E-C process which results in substantially stoichiometric methylation of the hindered $N^4$ or $N^5$-atom of the starting amine without using more than a 50% molar excess of HCHO, present either as aqueous formaldehyde or substantially anhydrous paraformaldehyde; and, sufficient formic acid to form a solution of the starting amine under the conditions at which it is methylated. Whether under "dilute" or "concentrated" conditions, all the water, including the water formed during the reaction, may remain in the reaction mass; or, some or most of the water may be separated during the reaction if the reaction mass is to be concentrated while the reaction proceeds. In either case, there is a single liquid phase present before the excess formic acid is neutralized and the reaction mass basified.

It has also been discovered that the foregoing starved E-C process produces a methylated DCA or DCA-containing complex amine which typically has so low a solubility in water under the alkaline conditions prevailing upon basifying the reaction mass, that methylated amine which separates may be washed with water with the loss of less than 5%, and preferably less than 1% of the methylated product.

It is therefore another object of this invention to provide a starved E-C process in which, under concentrated conditions, (a) solid paraformaldehyde is substituted for aqueous formaldehyde; (b) the amount of concentrated aqueous formic acid (at least 88% by weight HCOOH) is only sufficient to form a saturated solution of the starting amine under the temperature and pressure conditions of the reaction; (c) the methylation is carried out at or below reflux temperature so that the starting amine is substantially stoichiometrically converted; (d) after neutralization with excess aqueous alkali, the methylated amine separates from the reaction mass; (e) separated methylated amine is then washed with water without transferring more than 5% by wt, preferably less than 1% by wt, of the methylated product to the aqueous phase; and, (e) the yield of the methylated amine is at least 90%, and preferably 95% or more.

It is a specific object of this invention to provide the foregoing starved E-C process wherein the molar ratio of the >NH group(s) in the DCA or DCA-substituted compound and HCHO is in the range from about 1:1 to about 1:1.5, preferably in the range from 1:1.02 to 1:1.5, and most preferably from 1:1.05 to 1:1.2.

It is yet another specific object of this invention to provide the foregoing starved E-C process for the methylation of each hindered $N^4$ or $N^5$-atom in the diaza ring of a DCA or DCA-substituted compound, the process being carried out in an oxygen-free reaction zone operating at relatively low, preferably autogenously developed pressure at the temperature of reaction.

It is a further specific object of this invention to provide the foregoing starved E-C process comprising (a) operating a reaction zone at or below the boiling point of the reactants in solution and at autogeneous pressure, said zone containing only as much HCOOH as is required to dissolve the starting amine under reaction conditions, and less than a 50% molar excess of HCHO theoretically required to methylate only the amine >NH groups (the amide NH group in the DCA cannot be methylated) in the starting amine; (b) maintaining the conditions of reaction until essentially stoichiometrically complete methylation is obtained; (c) thereafter neutralizing the reaction mass so as to precipitate methylated amine product; and, (d) separating and washing the product with water, yet removing in the water) less than 1% by weight of the product.

BRIEF DESCRIPTION OF THE DRAWING

The foregoing and other objects and advantages of our invention will appear more fully from the following description, made in connection with the accompanying flowsheet of a preferred embodiment of the invention, illustrating a single multi-purpose reactor and associated equipment, in which reactor a DCA or DCA-substituted compound is methylated.

DETAILED DESCRIPTION OF PREFERRED EMBODIMENTS

It will now be evident that use of only a bare excess of HCHO, and sometimes only an equimolar amount, equal to the number of NH groups in the starting amine, permits the essentially complete conversion of the DCA or DCA-substituted compound to be methylated. This is attributable to the unique characteristics of the 2-keto group in the DCA. Also evident is that, because the reaction mass must be water-washed to remove the unreacted HCHO, HCOOH, and unwanted by-products, it is fortuitous that, not only does the desired methylated amine product separate spontaneously upon neutralization of the reaction mass, but that the product is essentially insoluble in water.

By "essentially complete conversion" I refer to methylation of at least 95%, and preferably 99% of the NH groups in the starting amine. By "essentially insoluble" I mean that the solubility is less than 1 part of product per 100 parts of water, so that upon washing, less than 1% by weight of the product recovered after neutralization of the reaction mass, is lost in the water wash.

It is most preferred, to save on the cost of recovering unreacted excess HCOOH, to use only as much as is necessary to solvate the complex (starting) amine at the temperature at which the reaction is to be carried out, provided that at least 1 mol of HCOOH is used for each NH group to be methylated. With many complex amines, from 1 to 2 mols of HCOOH will suffice for each >NH group to be methylated. Thus, the starved E-C reaction is starved not only of HCHO but also of HCOOH relative to the amounts used in a conventional E-C reaction.

To minimize the amount of water in the reaction, it is preferred to use paraformaldehyde and conc HCOOH which is at least 88% HCOOH, and preferably 95-97% HCOOH.

The general structure of a polysubstituted diazacycloalkan-2-one ("DCA") which is so effectively methylated in my process is represented by

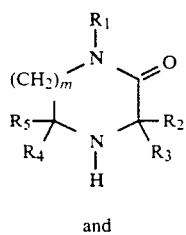
(IA)

and

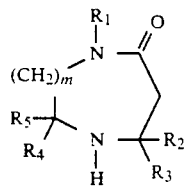
(IB)

wherein, m represents an integer in the range from 1 to 6, being the number of methylene groups some of which, (a) together with the carbons to which they are bound, may form a cyclopentyl, cyclohexyl or cycloheptyl endo ring, or (b) be substituted; when m is 1 then (I) represents a polysubstituted piperazin-2-one moiety, and when m is 5, and two of the methylene groups of the diaza ring are cyclized with four methylene groups to form a fused six-membered ring, then (I) typically represents a polysubstituted 2-keto-decahydroquinoxaline;

$R_1$ independently represents hydrogen, $C_1$-$C_{24}$ alkyl, $C_1$-$C_{12}$ aminoalkyl or iminoalkyl, and $C_1$-$C_{12}$ hydroxyalkyl; and when (I) is a substituent, $R_1$ represents a bond to an amine;

$R_2$, $R_3$, $R_4$ and $R_5$ independently represent $C_1$-$C_{24}$ alkyl; and, $R_2$ with $R_3$, or $R_4$ with $R_5$, together cyclized, form $C_5$-$C_7$ cycloalkyl.

The best mode of our process relates to methylation of PSPs such as those disclosed in aforementioned Japanese No. 63-86711 and U.S. Pat. Nos. 4,167,512; 4,190,751; 4,304,712; 4,309,336; 4,415,684; 4,480,092; 4,629,752; 4,639,479 and 4,780,495, the disclosures of which are incorporated by reference thereto as if fully set forth herein. Only the hindered $N^4$- or $N^5$-atom of each NH group, is methylated.

Illustrative PSPs in which the $N^4$-atom is methylated are represented by the structures:

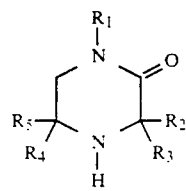
(II)

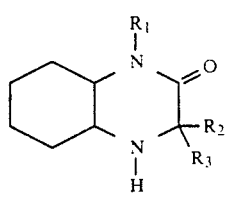
(III)

wherein, $R_2$, $R_3$, $R_4$ and $R_5$ independently represent —$CH_3$ or —$C_2H_5$; and when $R_2$ and $R_3$, or $R_4$ and $R_5$ are cyclized, each represents a pentamethylene spiro substituent; and, $R_1$ is selected from —$CH_3$; —$C_2H_5$; —CO—$CH_3$ and —CO—$C_6H_5$; Particular PSPs are illustrated by the following:

1-[3-(isopropylamino)propyl]-3,3,5,5-tetramethylpiperazin-2-one;
1-[2-(isopropylamino)ethyl]-3,3,5,5-tetramethylpiperazin2-one;
1-[2-(butylamino)ethyl]-3,3,5,5-tetramethylpiperazin-2one; and,
1-[2-(cyclohexylamino)ethyl]-3,3,5,5-tetramethylpiperazin2-one; inter alia.

Examples of particular PSPs (III) are: trans-3,3-pentamethylene-decahydro-2-quinoxalinone; and, 3-hexyl-3-methyl-cis-decahydroquinoxalin-2-one.

Other PSP-containing compounds have the structure:

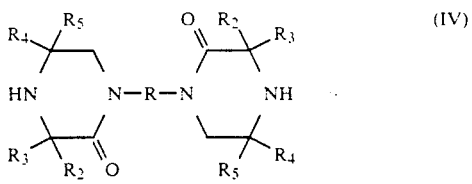
(IV)

wherein, $R_2$, $R_3$, $R_4$ and $R_5$ independently represent —$CH_3$ or —$C_2H_5$; and when $R_2$ and $R_3$, or $R_4$ and $R_5$ are cyclized, each represents a pentamethylene spiro substituent; and, R is selected from —$(CH_2)_n$ wherein n is an integer from 1 to 6; —CO—$(CH_2)_4$—CO— and —$CH_2$—$C_6H_4$—$CH_2$—.

Particular PSPs are 1,2-ethane-bis-(Nl-3,3,5,5-tetramethyl-piperazin-2-one) and 1,1'-(1,4-p-xylene)-bis(3,3,5,5-tetramethyl-piperazin-2-one). Similarly bis compounds of decahydroquinoxalin-2-one may be methylated. A particular such compound is 1,1'-(1,4-p-xylene)-bis-(3,3-pentamethylene-decahydroquinoxalin-2-one).

Illustrative 1,4- and 1,5-diazepin-2-ones in which the $N^4$- and $N^5$-atoms respectively, are methylated are represented by the structures:

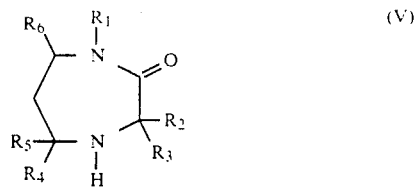
(V)

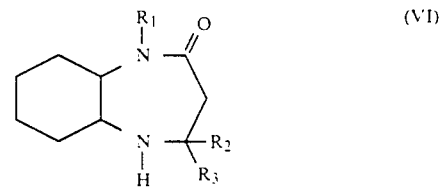
(VI)

wherein, $R_6$ has the same connotation as $R_2$, $R_3$, $R_4$ and $R_5$ hereinabove, and $R_1$ is the same as before.

Particular compounds (V) and (VI) are as follows:
$N^1$-(butyl)-3,3,5,5,7-pentamethyl-1,4-diazepin-2-one;

N¹-(butyl)-3,3-pentamethylene-5,5,7-trimethyl-1,4-diazepin-2-one;
4,4-dimethyl-decahydrobenzo-1,5-diazepin-2-one; and,
4,4-pentamethylene-decahydrobenzo-1,5-diazepin-2-one.

Bis-(1,4- and 1,5-diazepin-2-ones), similar to structure (IV) for PSPs, may also be methylated. Particular bis-1,4-diazepin-2-one compounds are: 1,2-ethane-bis-(N¹-3,3,5,5,7-pentamethyl-1,4-diazepin-2-one); 1,2-ethane-bis-(N¹-(butyl)-3,3-pentamethylene-5,5,7-trimethyl-1,4-diazepin-2-one; and, 1,4-p-xylene-bis-(3,3-pentamethylenedecahydroquinoxalin-2-one). Particular bis-(1,5-diazepin-2-ones) are 1,2-ethane-bis-(N¹-4,4,6,6-tetramethyl-1,5-diazepin-2-one) and 1,1'-(1,4-p-xylene)-bis-(4,4,6,6-tetramethyl-1,5-diazepin-2-one). Similarly bis compounds of decahydrobenzo-1,5-diazepin-2-one may be methylated.

PIP-Ts are typically prepared by substituting at least one, and most preferably, each of two or three chlorine (or other halogen) atoms on a di- or trihalo-s-triazine, specifically cyanuric chloride, with a PSP, so as to form a substituted triazine. Such PIP-T compounds in which the diazacycloalkane ring is connected to the triazine ring through an alkyleneimine linkage (hence termed "distally connected"), are identified more fully herebelow for illustrative purposes, and in the foregoing '092, '752 and '479 patents.

A preferred substituted triazine is represented by the structure

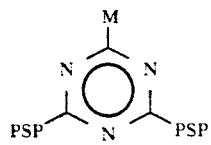
(VII)

wherein PSP represents a substituent selected from the group consisting of structures

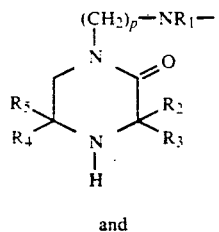
(VIII)

and

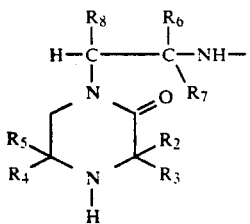
(IX)

wherein, $R_1$ is $C_1$-$C_{24}$ alkyl, $C_5$-$C_{12}$ cycloalkyl, phenyl, $C_7$-$C_{20}$ aralkyl, $C_1$-$C_{24}$ azaalkyl, and $C_6$-$C_{20}$ azacycloalkyl;

$R_2$, $R_3$, $R_4$, and $R_5$ independently represent $C_1$-$C_{24}$ alkyl; $R_6$, and $R_7$ independently represent $C_1$-$C_{24}$ alkyl and polymethylene having from 4 to 7 C atoms which are cyclizable; and, p represents an integer in the range from 2 to about 10;

$R_8$ represents H, $C_1$-$C_6$ alkyl and phenyl; and M may be the same as PSP or a bond to the N atom of any amine.

Other preferred PIP-Ts are represented by structures:

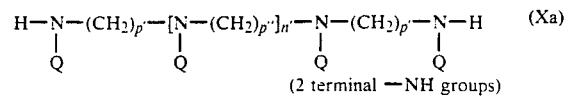
(Xa)
(2 terminal —NH groups)

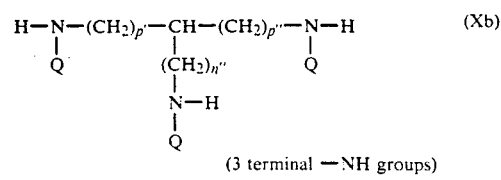
(Xb)
(3 terminal —NH groups)

and

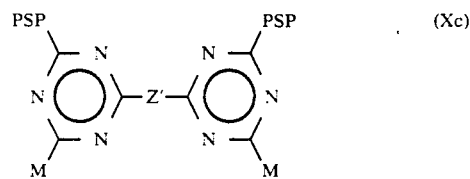
(Xc)

wherein n' represents an integer from 0 to 6; n" is 0 or 1;

p' and p" independently represent an integer in the range from 2 to about 20;

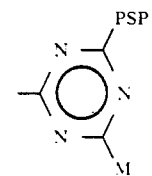

Z' represents

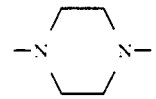

or —HN—(CH₂)ₚ—NH— M represents —(Bu)₂ where Bu=butyl,

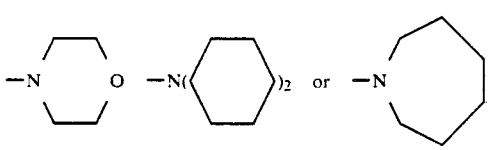

and, M may be the same PSP.

The terminal —NH groups in the foregoing PIP-Ts are generally not methylated under the conditions of the starved E-C process.

A particular PIP-T is formed by the reaction of cyanuric chloride with a particular PSP amine reactant, 1-[3-(cyclohexylamino)propyl]-3,3,5,5-tetramethylpiperazin-2-one, familiarly referred to as cyclohexylpiperazinone, ("CHP" for brevity), represented by the structure:

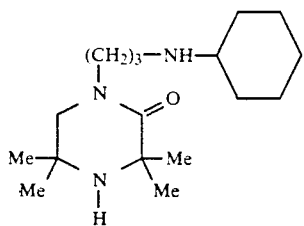
(XI)

The structure of the PIP-T which is to be methylated is represented as follows:

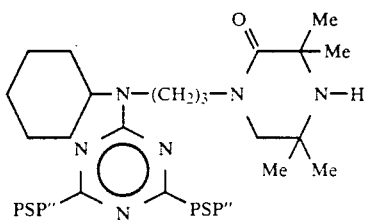
(XII)

wherein PSP" represents the same structure written for the other substitutent.

The structure of the desired methylated PIP-T product is represented as follows:

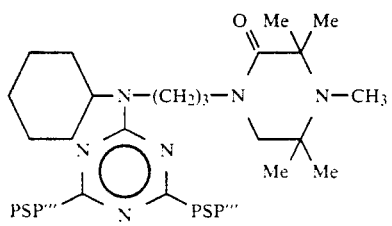
(XIII)

wherein PSP'" represents the same structure written for the other substituent.

Crystallizable triazines with other PSP moieties as substituents, whether di- or tri-substituted, may also be methylated as described. The PIP-Ts are formed by reaction of cyanuric chloride with the following polysubstituted piperazin-2-ones:

1-[3-(isopropylamino)propyl]-3,3,5,5-tetramethylpiperazin-2-one;
1-[2-(isopropylamino)ethyl]-3,3,5,5-tetramethylpiperazin-2-one;
1-[2-(butylamino)ethyl]3,3,5,5-tetramethylpiperazin-2-one; and,
1-[2-(cyclohexylamino)ethyl]-3,3,5,5-tetramethylpiperazin-2one; inter alia.

3,5-DHPZNA compounds which may be methylated are N-(substituted)-1-(piperazin-2-onealkyl)-α-(3,5-dialkyl-4-hydroxyphenyl)-α,α-substituted acetamides, represented by the structure

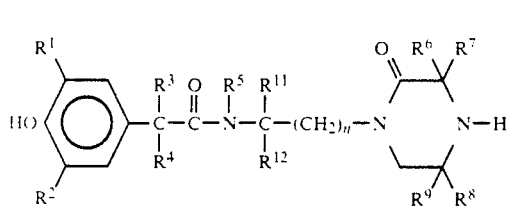
(XIV)

wherein, $R^1$, $R^2$ and $R^5$ each represent hydrogen, $C_1$-$C_{12}$ alkyl, phenyl, naphthyl, $C_4$-$C_{12}$ cycloalkyl, and, alkylsubstituted cycloalkyl, phenyl and naphthyl, each alkyl substituent being $C_1$-$C_8$, and at least one of $R^1$ and $R^2$ is t-$C_4$-$C_{12}$ alkyl;

$R^3$ and $R^4$ independently represent $C_1$-$C_{18}$ alkyl, and $C_5$-$C_{12}$ cycloalkyl, phenyl and naphthyl, and, alkyl-substitute cycloalkyl, phenyl and naphthyl, each alkyl substituent being $C_1$-$C_8$, and, when together cyclized, $R^3$ with $R^4$ may represent $C_4$-$C_{12}$ cycloalkyl, and $C_1$-$C_8$ alkyl-substituted cycloalkyl;

$R^6$, $R^7$, $R^8$ and $R^9$ each represent $C_1$-$C_{12}$ alkyl, or, when together cyclized, $R^6$ with $R^7$, and $R^8$ with $R^9$, may represent $C_4$-$C_{12}$ cycloalkyl, and $C_1$-$C_8$ alkyl-substituted cycloalkyl;

$R^{11}$ and $R^{12}$ independently represent hydrogen and $C_1$-$C_{18}$ alkyl; and, n is an integer in the range from 1 to about 8. The foregoing compounds are made as taught in the aforementioned '479 U.S. patent. Illustrative of such compounds are the following:

N-isopropyl-N-[2-(2-keto-3,3,5,5-tetramethyl-1-piperazinyl)ethyl]-2-(3,5-di-t-butyl-4-hydroxyphenyl)-2-methylpropanamide represented by the structure

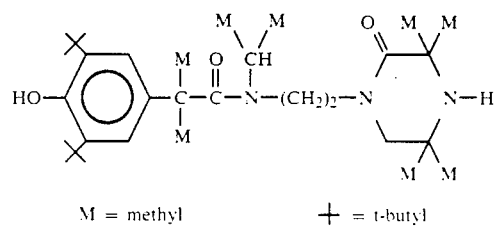

M = methyl     + = t-butyl

N-[1-(2-keto-3,3,5.5-tetremethyl-1-piperazinyl-2-methyl-2-propyl]-2-(3,5-di-to-butyl-4-hydroxyphenyl)-2-methyl-propanamide represented by the structure

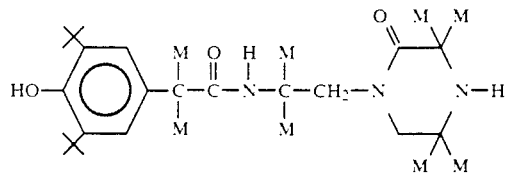

N-[1-(2-keto-3,3-pentamethylene-5,5-dimethyl-1-piperazinyl) -2-methyl-2-propyl]-2-(3,5-di-t-butyl-4-hydroxyphenyl) -2,2-pentamethylene acetamide represented by the structure

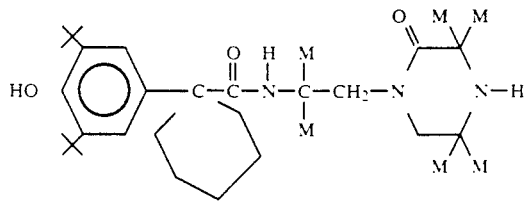

N-[1-(2-keto-3,3,5,5-tetramethyl-1-piperazinyl-2-methyl 2-propyl]-2-(3,5-di-t-butyl-4-hydroxyphenyl)-2,2-pentamethylene acetamide represented by the structure

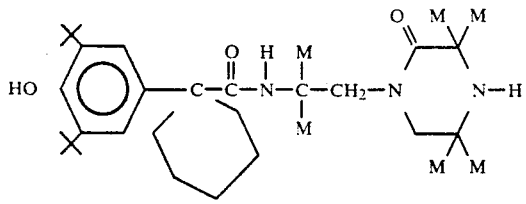

N-cyclohexyl-N-[2-(2-keto-3,3,5,5-tetramethyl-1-piperazinyl ethyl]-2-(3,5-di-t-butyl-4-hydroxyphenyl)-2,2-pentamethylene acetamide represented by the structure

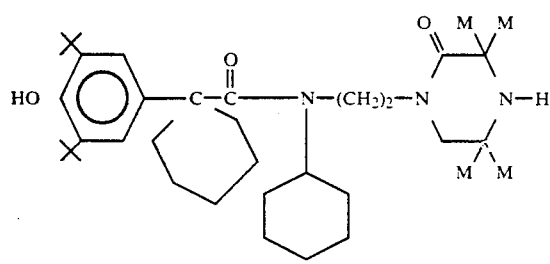

The processing aspects of the starved E-C reaction compared to those of a conventional E-C reaction will be more fully recognized in the following illustrative examples in which complex amines with the following structures:

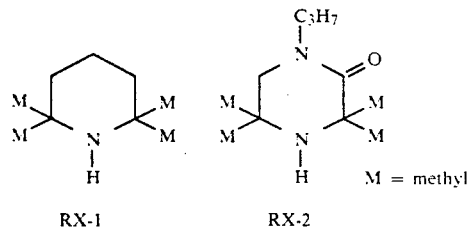

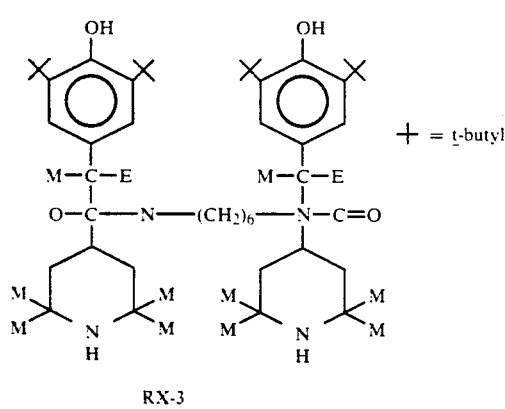

-continued

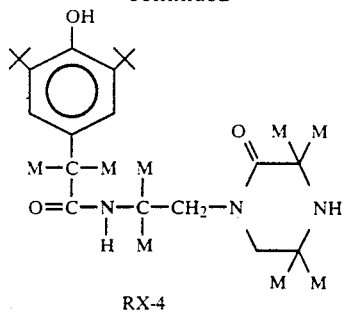

RX-4

In the following illustrative examples, the methylated PSP-containing product was produced essentially stoichiometrically within about 8 hr. It was thereafter washed repeatedly, the slurry centrifuged and the waterwet cake dried in an oven. Because of the difficulty of removing small quantities of moisture, and to produce product with less than 100 ppm moisture, it is sometimes desirable to dry the recovered product in an oven, then dissolve the dried product in a good solvent such as methylene chloride or other halohydrocarbon. Bone-dry product (less than 100 ppm. and preferably less than 10 ppm water) is then precipitated from the solution, for example, by adding a precipitation agent such as heptane/toluene mixture.

As an alternative, the methylene chloride solvent may be added before the methylated product is dried, and the organic phase separated from the aqueous phase. The product is then precipitated from the organic phase, as before.

EXAMPLE 1

Conventional E-C reaction of 2,2,6,6-tetramethyl-4-piperidine (RX-1) using a 2-fold molar excess of HCHO and 4-fold molar excess of HCOOH:

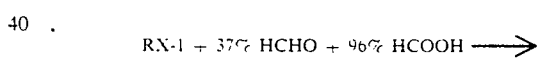

|  |  |  |  |
|---|---|---|---|
| mol used | 1.0 | 2.0 | 4.0 |
| mol wt. | 141.2 | 30 | 46 |
| amt used | 141.2 g | 162.1 g | 157. ml |

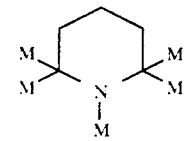

M = methyl

Into a three-neck, 3-liter round-bottomed flask fitted with a condenser, thermometer and mechanical stirrer, was placed about 130 ml 96% HCOOH and 141.2 g of the starting amine to be methylated. An additional 27 ml of starting amine to be methylated. An additional 27 ml of the 96% HCOOH was used to rinse starting amine remaining on the funnel into the flask which is heated to about 80° C., at which temperature all the starting amine was dissolved. Then 162.1 g of 37% formaldehyde is gradually added to the flask and the contents heated to 95° C. After about 3 hr, the reaction was continued under reflux conditions at atmospheric pressure. After refluxing for about 12 hr the reaction mass is worked up by removing water distilled over thus concentrating the reaction mass. The mixture is then basified with 50% aqueous NaOH, further concentrated and precipitated by the addition of methylene chloride.

Conversion to the pentamethyl-piperidine was essentially complete (about 99%) and the yield after recrystallization from a heptane/toluene mixture is about 90%.

EXAMPLE 2

Starved E-C reaction of 2,2,6,6-tetramethyl-4-piperidine (RX-1) using a 1.5-fold (50%) molar excess of 37% HCHO and 4-fold molar excess of 96% HCOOH:

In a manner analogous to that described immediately hereinabove, the reaction is carried out with only a 50% molar excess of HCHO. The reaction mass was difficult to work up. Upon NMR analysis of the reaction mass it is found that less than 50 mol% of the starting amine was converted to pentamethyl-piperidine.

EXAMPLE 3

Conventional E-C reaction of $N^1$-propyl-3,3,5,5-tetramethyl-piperazin-2-one (RX-2) using a 2.4-fold molar excess of 37% HCHO and 25.4-fold molar excess of 96% HCOOH:

RX-2 + 37% HCHO + 96% HCOOH ⟶ methylated RX-2

|          | RX-2   | HCHO   | HCOOH   |
|----------|--------|--------|---------|
| mol wt.  | 970    | 30     | 46      |
| amt used | 421.2  | 84.3 g | 1 liter |
| mol      | 0.4342 | 1.04   | 25.4    |

In a manner analogous to that described hereinabove 900 ml 96% HCOOH and 421.2 g of the starting amine RX-2 was added to the flask through a funnel. An additional 100 ml HCOOH was used to rinse a little RX-1 remaining on the funnel all being dissolved in the HCOOH as the flask is heated to about 80° C. Then the 37% HCHO is gradually added to the flask and the contents heated to 95° C. After about 3 hr, the reaction was continued under reflux conditions. After refluxing for 0.5 hr the heating mantle was dropped to allow the flask to cool and an additonal 24 g (0.8 mol) of paraformaldehyde added. The reaction was continued under reflux for an additional 12 hr, and the reaction mass worked up by concentrating it to remove most of the HCOOH. The mixture is then basified with 50% aqueous NaOH. Because of difficulty separating the methylated product, methylene chloride is added to dissolve the methylated RX-2 and form an organic layer which is separated, washed with saturated NaCl solution and dried overnight.

Conversion of the RX-2 to 3,3,4,5,5-pentamethylpiperazin-2-one was essentially complete (about 99 mol%) and the yield is about 90%.

EXAMPLE 4

Starved E-C reaction of N1-propyl-2,2,6,6-tetramethylpiperazin -2-one (RX-2) using a 1.4-fold (40%) molar excess of 37% HCHO and 4-fold molar excess of 96% HCOOH:

In a manner analogous to that described immediately hereinabove, the reaction is carried out with only a 40% molar excess of HCHO. Upon basifying the reaction mass pentamethyl-piperazinone separates as a solid. Upon filtration, less than 1 mol% is found in the filtrate. Upon recrystallization of the solid from heptane it is found that the yield is about 99 mol%. Comparable results are obtained when only 1.9 mols (90% excess) of HCOOH are used.

EXAMPLE 5

Starved E-C reaction of RX-3 using a 50% excess of 37% HCHO and 5-fold excess of 96% HCOOH:

The compound RX-3 was methylated in a manner analogous to that described hereinabove, except that only a 50% molar excess of HCHO was used. Upon concentration of the reaction mass, after the reaction was run for the same time as that in example 4 above, a thick oil was formed. Upon basifying with aqueous NaOH no product separates from the reaction mass. Efforts to separate methylated product from the oily mass were unsuccessful, so the thick oil was analyzed. The NMR mass spectra showed the presence of methylated >NH groups in the product, but less than 50% of the RX-3 was converted to methylated product.

EXAMPLE 6

Starved E-C reaction of RX-4 using a 50% excess of 37% HCHO and 5-fold excess of 96% HCOOH:

A comparison is made with RX-3 because there is no practical way to make a PSP-substituted compound corresponding to RX-3. The PSP-substituted complex amine RX-4 represented by the structure hereinabove is a closely analogous (to RX-3) structure for the purpose of this comparison.

The compound RX-4 was methylated in a manner analogous to that described in example 5 hereinabove. Upon concentration of the reaction mass, after the reaction was run for the same time as that in example 5 above, a clear syrup is obtained. Upon basifying with aqueous NaOH a white product separates from the reaction mass. Upon washing repeatedly with water and drying, methylated RX-4 is recovered with an yield of about 95 mol%. Analysis of the filtrate indicates that less than 1 mol% of the RX-4 rremains unconverted, indicating essentially complete (99 mol%) conversion.

EXAMPLE 7

In a manner analogous to that described hereinabove, the PIP-T (XII) was methylated under starved E-C conditions, as follows:

PIP-T + 37% HCHO + 90% HCOOH ⟶ methylated PIP-T 0.6 mole   2.16 moles   6.48 moles      XIII 0.6 mole To a 5 liter reactor is charged 289 g (0.3 mole) PIP-T XII, 64.9 g of HCHO (in 37% solution) and 313.9 g of formic acid (in 90%). The mixture is heated to 65° C. with stirring and when the temperature reaches about 80° C., the remaining PIP-T is added. The temperature of the reaction mass is raised to about 102° C. and the reaction monitored by liquid chromatographic (LC) analysis, to monitor the disappearance of the PIP-T. Since there is a substantial amount of XII remaining after 8 hr, the reaction is continued until essentially all the XII has disappeared, which takes about 12 hr.

The reaction mass obtained is a colored oil which, when cooled to room temperature, is highly viscous. To precipitate the methylated product from this oil, it is heated to about 80° C. and 1 liter of water added to obtain a slurry having a pH of about 3. When this slurry is neutralized with a large excess of 25% NaOH solution, a foamy solid is precipitated.

To work up this solid, the neutralized solution is filtered. The aqueous filtrate contains a substantial amount of XIII which does not precipitate. The white filter cake (965 g) is washed with about 2 liter of demineralized (DM) water in a 5 liter flask, and filtered.

After washing repeatedly to remove HCHO and formate, the washed cake is dried to yield 478 g of essentially pure methylated product. Since theoretical yield is 604.2 g it is evident that the solubility of the methylated PIP-T is substantial enough to necessitate the recovery of product remaining in both the aqueous alkaline filtrate as well as the first water wash.

The filtrate and water wash are heated with an additional amount of 25% NaOH to precipitate more solid which is washed and dried as before, to yield 102 g of product. Recovery of a total of 580 g of product represents a yield of 96%.

The process is schematically illustrated in the Figure in which a reaction vessel 10 provides a reaction zone for obtaining essentially complete conversion of a DCA-containing compound with a starved E-C procedure. In the first step, the HCOOH is charged as a 96% HCOOH aqueous solution. The DCA is added to the reactor and the contents are heated to reaction temperature while stirring so that the DCA dissolves. The first step is identified by reference numeral 1, written in a circle to distinguish the symbol from numerals used to identify equipment.

In the second step (identified as step 2), the HCHO, preferably as paraformaldehyde, is gradually added and the reaction conditions maintained until the reaction is complete. To concentrate the solution and to speed up the reaction, it is completed under reflux (step 3), water being withdrawn from the reflux condenser 11. A surge tank 12 is provided for safety reasons. The reaction is tracked by periodic analysis of the reactor's contents.

After the reaction is complete, neutralization of the contents of the reactor either with a solution of an alkali metal hydroxide or ammonium hydroxide (step 4), results in separation of a water-insoluble (in non-alkaline water) methylated amine in an aqueous alkaline slurry, if the solution has been sufficiently concentrated. Typically, methylated DCA is precipitated as solid by cooling hot super-saturated alkaline solution. The supernatant solution of HCHO and formate, along with impurities and unwanted byproducts is conveniently drained (step 5) from the reactor. The separated solid is washed with distilled water (step 6), several times if necessary, to remove the formate and unreacted paraformaldehyde, and any water-soluble byproducts which may be formed. The wash water is drained from the reactor in step 7.

As shown in the Figure, concentration of the solution is done prior to neutralization but may also be done after neutralization, if desired. Further, the methylation reaction, precipitation of the methylated DCA, and washing out the unreacted formaldehyde, the formate formed after neutralization, and other impurities, are shown as being done in the reactor to avoid transferring the contents of the reactor (after the reaction is completed), to another vessel(s) for "work-up" and recovery of the essentially pure methylated DCA.

It is preferred to use the reactor solely for carrying out the methylation reaction, and to work-up the formate solution in which the methylated DCA is dispersed, in separate unit operations.

The slurry from the reactor is flowed to a centrifuge 13, in which the centrifuged solids may be further washed with successive water washes to free the cake from impurities. The wet cake from the centrifuge is then dried in a vacuum oven 14. The dried product, essentially free of contaminants, is then transferred to suitable containers.

Since the main use of the methylated DCAs is in polyacetals and polyamides to stabilize them against degradation due to heat and particularly to light, it is generally required that the product be bone-dry not only with respect to water, but also with respect to solvent. The latter being more easily removed than the former, a purification step, as described hereinabove, precipitating the product from a solvent, is generally desirable.

Further, for economic reasons, as little excess of HCHO and HCOOH are used as will yield essentially complete conversion to the methylated product. As might be expected, some DCAs might provide better reactor productivity (pounds product/unit volume of reactor) with more than 1.5 mol HCHO per >NH group, but the ratio will always be less than 2. Similarly, though less than 2 mols of HCOOH will preferably be used per >NH group, more than 2 may improve productivity. The higher the temperature of reaction the better, as long as the temperature is below that at which at least 90% by weight of the complex amine is converted to methylated product, and the generation of impurities is kept to a minimum. The operating pressure is generally about atmospheric but may be as high as 5 atm if such high pressure is economically justified.

I claim:

1. A process for methylating a complex amine including at least one polysubstituted diazacycloalkan-2-one ring containing a hindered nitrogen atom, comprising,
   (a) reacting (i) said complex amine with (ii) formaldehyde or paraformaldehyde, in amounts such that the molar ratio of NH groups : HCHO is in the range from about 1:1 to 1:1.5, and (iii) at least sufficient formic acid to dissolve said complex amine under the conditions of reaction;
   (b) maintaining a temperature above about 60° C. but below a temperature at which more than 10% by weight of said complex amine is converted to byproducts, so as to form a solution of methylated complex amine in the reaction mass;
   (c) neutralizing unreacted formic acid with an excess of aqueous alkaline solution so as to separate methylated complex amine as product;
   (d) separating said product from said aqueous alkaline solution; and,
   (e) washing water-soluble impurities from said product;
whereby said hindered nitrogen atom is essentially stoichiometrically quantitatively methylated.

2. The process of claim 1 wherein said complex amine is represented by a structure represented by

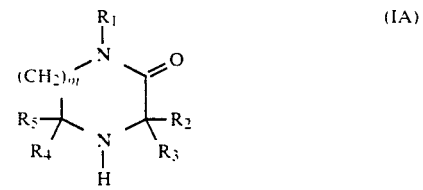

and

-continued

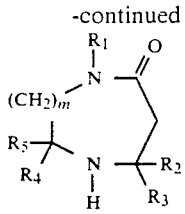 (IB)

wherein, m represents an integer in the range from 1 to 6, being the number of methylene groups some of which, (a) together with the carbons to which they are bound, may form a cyclopentyl, cyclohexyl or cycloheptyl endo ring, or (b) be substituted; when m is 1 then (I) represents a polysubstituted piperazin-2-one moiety, and when m is 5, and two of the methylene groups of the diaza ring are cyclized with four methylene groups to form a fused six-membered ring, then (I) typically represents a polysubstituted 2-keto-decahydroquinoxaline;

$R_1$ independently represents hydrogen, $C_1$-$C_{24}$ alkyl, $C_1$-$C_{12}$ aminoalkyl or iminoalkyl, and $C_1$-$C_{12}$ hydroxyalkyl; and when (I) is a substituent, $R_1$ represents a bond to an amine;

$R_2$, $R_3$, $R_4$ and $R_5$ independently represent $C_1$-$C_{24}$ alkyl; and, $R_2$ with $R_3$, or $R_4$ with $R_5$, together cyclized, form $C_5$-$C_7$ cycloalkyl.

3. The process of claim 1 wherein said complex amine is a piperazin-2-one represented by a structure
wherein, $R_2$, $R_3$, $R_4$ and $R_5$ independently represent —$CH_3$ or —$C_2H_5$;

R2 with R3, or R4 with R5 are cyclized, form $C_5$-$C_7$ cycloalkyl; and, $R_1$ is selected from —$CH_3$; —$C_2H_5$; —CO—$CH_3$ and —CO—$C_6H_5$.

4. The process of claim 1 wherein said complex amine is a member of the group selected from a 1,4-diazepin-2-one and a 1,5-diazepin-2-one represented by

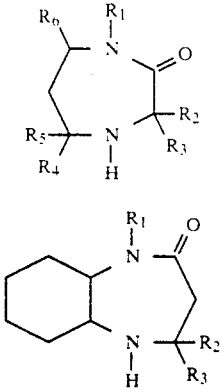

wherein $R_2$, $R_3$, $R_4$, $R_5$, and $R_6$ independentyl represent —$CH_3$ or —$C_2H_5$;

$R_2$ with $R_3$, or $R_4$ with $R_5$ are cyclized, form $C_5$-$C_7$ cycloalkyl; and, $R_1$ is selected from —$CH_3$; —$C_2H_5$; —CO—$CH_3$ and —CO—$C_6H_5$.

5. The process of claim 1 wherein said complex amine is represented by a triazine compound having at least one piperazine-2-one substituent, represented by a structure selected from

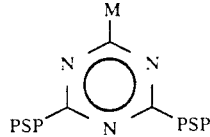 (II)

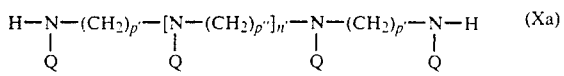 (Xa)

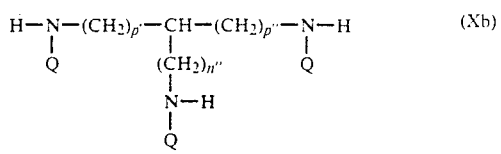 (Xb)

and

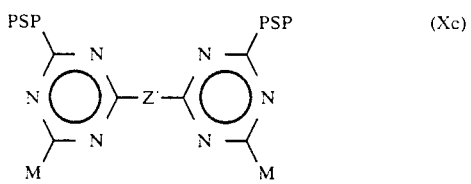 (Xc)

wherein PSP represents a substituent selected from the group consisting of structures

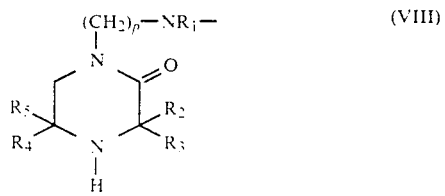 (VIII)

and

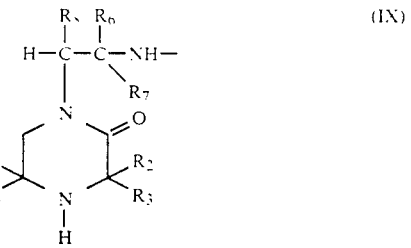 (IX)

$R_1$ represents $C_1$-$C_{24}$ alkyl, $C_5$-$C_{12}$ cycloalkyl, phenyl, $C_7$-$C_{20}$ aralkyl, $C_1$-$C_{24}$ azaalkyl, and $C_6$-$C_{20}$ azacycloalkyl; $R_2$, $R_3$, $R_4$, and $R_5$ independently represent $C_1$-$C_{24}$ alkyl; $R_6$, and $R_7$ independently represent $C_1$-$C_{24}$ alkyl and polymethylene having from 4 to 7 C atoms which are cyclizable; $R_8$ represents H, $C_1$-$C_6$ alkyl and phenyl; and M may be the same as PSP or a bond to the N atom of an amine;

n' is an integer from 0 to 6; n" is 0 or 1;

p represents an integer in the range from 2 to about 10;

p' and p" independently represent an integer in the range from 2 to about 20;

Q represents $$-N\underset{M}{\overset{PSP}{\diagdown}}\underset{N}{\overset{N}{\bigcirc}}N$$

Z' represents $$-N\diagdown\diagup N-$$

or —HN—(CH$_2$)$_p$—NH—M represents -N(Bu)$_2$ where Bu=butyl, $$-N\diagdown\diagup O \quad -N(\diagdown\diagup)_2 \text{ or } -N\diagdown\diagup$$

and, M may be the same as PSP.

6. The process of claim 1 wherein said complex amine is represented by a N-(substituted)-1-(piperazin-2-onealkyl)-(3,5-dialkyl-4-hydroxyphenyl)- α, α-substituted acetamide, represented by the structure

[Structure: 3,5-DHPZNA]

wherein, R$^1$, R$^2$ and R$^5$ each represent hydrogen, C$_1$-C$_{12}$ alkyl, phenyl, naphthyl, C$_4$-C$_{12}$ cycloalkyl, and, alkylsubstituted cycloalkyl, phenyl and naphthyl, each alkyl substituent being C$_1$-C$_8$, and at least one of R$^1$ and R$^2$ is t-C$_4$-C$_{12}$ alkyl;

R$^3$ and R$^4$ independently represent C$_1$-C$_{18}$ alkyl, and C$_5$-C$_{12}$ cycloalkyl, phenyl and naphthyl, and, alkyl-substituted cycloalkyl, phenyl and naphthyl, each alkyl substitutuent being C$_1$-C$_8$, and, when together cyclized, R$^3$ with R$^4$ may represent C$_4$-C$_{12}$ cycloalkyl, and C$_1$-C$_8$ alkyl-substituted cycloalkyl;

R$^6$, R$^7$, R$^8$ and R$^9$ each represent C$_1$-C$_{12}$ alkyl, or, when together cyclized, R$^6$ with R$^7$, and R$^8$ with R$^9$, may represent C$_4$-C$_{12}$ cycloalkyl, and C$_1$-C$_8$ alkyl-substituted cycloalkyl;

R$^{11}$ and R$^{12}$ independently represent hydrogen and C$_1$-C$_{18}$ alkyl; and, n is an integer in the range from 1 to about 8.

7. The process of claim 1 wherein said formic acid is present as at least 88% formic acid in water.

8. The process of claim 2 wherein said complex amine paraformaldehyde, and formic acid are present in an amount such that the molar ratio of >NH groups : HCHO is in the range from about 1:1.02 to 1:1.5; and the molar ratio of >NH groups : HCOOH is in the range from above 1:1 but less than 1:2.

9. The process of claim 2 wherein said aqueous alkaline solution is of an alkali metal hydroxide or ammonium hydroxide.

10. The process of claim 3 wherein said complex amine is a polysubstituted piperazin-2-one selected from the group consisting of
   1-[3-(isopropylamino)propyl]-3,3,5,5-tetramethylpiperazin-2-one;
   1-[2-(isopropylamino)ethyl]-3,3,5,5-tetramethylpiperazin-2-one;
   1-[2-(butylamino)ethyl]-3,3,5,5-tetramethylpiperazin-2-one;
   1-[2-(cyclohexylamino)ethyl]-3,3,5,5-tetramethylpiperazin-2-one;
   trans-3,3-pentamethylene-decahydro-2-quinoxalinone; and,
   3-hexyl-3-methyl-cis-decahydroquinoxalin-2-one;
   1,2-ethane-bis-(N$^1$-3,3,5,5-tetramethyl-piperazin-2-one);
   1,1'-(1,4-p-xylene)-bis-(3,3,5,5-tetramethyl-piperazin-2-one); and,
   1,1'-(1,4-p-xylene)-bis-(3,3-pentamethylene decahydroquinoxalin-2-one).

11. The process of claim 4 wherein said complex amine is a polysubstituted 1,4-diazepin-2-one selected from the group consisting of
   N$^1$-(butyl)-3,3,5,5,7-pentamethyl-1,4-diazepin-2-one;
   N$^1$-(butyl)-3,3-pentamethylene-5,5,7-trimethyl-1,4-diazepin-2-one;
   1,2-ethane-bis-(N$^1$-3,3,5,5,7-pentamethyl-1,4-diazepin-2-one);
   1,2-ethane-bis-(N$^1$-(butyl)-3,3-pentamethylene-5,5,7-trimethyl-1,4-diazepin-2-one; and,
   1,4-p-xylene-bis-(3,3-pentamethylene-decahydroquinoxalin-2-one).

12. The process of claim 4 wherein said complex amine is a polysubstituted 1,5-diazepin-2-one selected from the group consisting of
   4,4-dimethyl-decahydrobenzo-1,5-diazepin-2-one;
   4,4-pentamethylene-decahydrobenzo-1,5-diazepin-2-one;
   1,2-ethane-bis-(N$^1$-4,4,6,6-tetramethyl-1,5-diazepin-2-one); and,
   1,1'-(1,4-p-xylene)-bis-(4,4,6,6-tetramethyl-1,5-diazepin-2-one).

13. The process of claim 1 wherein there is less than 30% by weight water in said reaction mass after methylation of said complex amine so that said process is carried out under concentrated conditions.

14. The process of claim 1 wherein there is more than 30% by weight water in said reaction mass after methylation of said complex amine so that said process is carried out under dilute conditions.

15. The process of claim 10 wherein formaldehyde is present as paraformaldehyde, and said polysubstittued piperazin-2-one substitutent, paraformaldehyde and formic acid are present in an amount such that the molar ratio of >NH groups : HCHO : HCOOH is in the range from about 1:1:1 to 1:1.5:2.

16. The process of claim 3 wherein said steps (a) through (c) are completed in less than 8 hr.

17. The process of claim 4 wherein said steps (a) through (c) are completed in less than 8 hr.

18. In a modified Eschweiler-Clarke process in which an excess of formaldehyde and at least 88% formic acid is used to methylate the >NH groups of a complex amine which includes a triazine ring substituted with at least one polysubstituted diazacycloalkan-2-one ("DCA") substituent, each said substituent having a hindered N atom flanked either by disubstituted carbon atoms, or carbon atoms having spiro substituents, the improvement comprising, (a) dissolving said complex amine under the conditions of reaction;

(b) reacting (i) said complex amine with (ii) said formaldehyde in an amount such that the molar ratio of >NH groups : HCHO is in the range from about 1:1 to 1:1.5 so as to obtain essentially quantitative conversion of said DCA substituent to methylated DCA-substituent;

(c) maintaining a temperature above about 60° C. but below a temperature at which 10% by weight of said complex amine is converted to byproducts;

(d) neutralizing unreacted formic acid with an excess of aqueous alkaline solution so as to precipitate methylated product;

(e) separating an aqueous phase of formate from said methylated product;

(f) washing said product with a non-alkaline aqueous wash so as to wash out water-soluble impurities and leave a wet product;

(g) drying the wet product and recovering said product in essentially pure form, in an yield in excess of 90%, said product having a water content of less than 100 ppm.

19. The process of claim 18 wherein formaldehyde is present as paraformaldehyde, and said polysubstittued piperazin-2-one substitutent, paraformaldehyde and formic acid are present in an amount such that the molar ratio of >NH groups : HCHO : HCOOH is in the range from about 1:1:1 to 1:1.5:2.

20. The process of claim 19 wherein there is less than 30% by weight water in said reaction mass after methylation of said complex amine so that said process is carried out under concentrated conditions.

21. The process of claim 19 wherein there is more than 30% by weight water in said reaction mass after methylation of said complex amine so that said process is carried out under dilute conditions

* * * * *